US012594186B2

(12) United States Patent
Jung et al.

(10) Patent No.: US 12,594,186 B2
(45) Date of Patent: Apr. 7, 2026

(54) AQUEOUS HUMOR DRAINAGE DEVICE WITH ADJUSTABLE TUBE DIAMETER

(71) Applicants: THE CATHOLIC UNIVERSITY OF KOREA INDUSTRY-ACADEMIC COOPERATION FOUNDATION, Seoul (KR); WONKWANG UNIVERSITY CENTER FOR INDUSTRY-ACADEMY COOPERATION, Iksan-si (KR)

(72) Inventors: Kyoung In Jung, Seoul (KR); Seung Jae Lee, Iksan-si (KR); Hun Jin Jeong, Iksan-si (KR); Nae Un Kang, Iksan-si (KR)

(73) Assignees: THE CATHOLIC UNIVERSITY OF KOREA INDUSTRY-ACADEMIC COOPERATION FOUNDATION, Seoul (KR); WONKWANG UNIVERSITY CENTER FOR INDUSTRY-ACADEMY COOPERATION, Iksan-si (KR)

( * ) Notice: Subject to any disclaimer, the term of this patent is extended or adjusted under 35 U.S.C. 154(b) by 461 days.

(21) Appl. No.: 18/013,117

(22) PCT Filed: Jun. 28, 2021

(86) PCT No.: PCT/KR2021/008097
§ 371 (c)(1),
(2) Date: Dec. 27, 2022

(87) PCT Pub. No.: WO2021/261973
PCT Pub. Date: Dec. 30, 2021

(65) Prior Publication Data
US 2023/0240892 A1 Aug. 3, 2023

(30) Foreign Application Priority Data
Jun. 26, 2020 (KR) ........................ 10-2020-0078634

(51) Int. Cl.
*A61F 9/007* (2006.01)
*A61M 25/00* (2006.01)

(52) U.S. Cl.
CPC .. *A61F 9/00781* (2013.01); *A61F 2210/0004* (2013.01); *A61F 2210/0066* (2013.01);
(Continued)

(58) Field of Classification Search
CPC .......... A61F 9/00781; A61F 2210/0004; A61F 2230/0006; A61F 2250/001; A61F 2250/0031
See application file for complete search history.

(56) References Cited

U.S. PATENT DOCUMENTS 4,946,436 A * 8/1990 Smith ................. A61F 9/00781
604/8
5,743,868 A * 4/1998 Brown ............... A61F 9/00781
604/9
(Continued)

FOREIGN PATENT DOCUMENTS

CN 104274865 A 1/2015
JP 2019-507660 A 3/2019
(Continued)

*Primary Examiner* — Leslie R Deak
(74) *Attorney, Agent, or Firm* — Bridgeway IP Law Group, PLLC; Jihun Kim

(57) ABSTRACT

Proposed is an aqueous humor drainage device with an adjustable tube diameter that is inserted into an eyeball to drain aqueous humor discharged from the eyeball to the outside, the aqueous humor drainage device comprising: an annular outer tube part having a predetermined thickness and having a hollow inside; and an annular inner tube part coupled to the inner surface of the outer tube part and having a predetermined thickness and a hollow inside, wherein the inner tube part has a shrinkage hole formed therein and is made of a biodegradable material.

13 Claims, 14 Drawing Sheets

100

(52) U.S. Cl.
CPC ................. *A61F 2230/0006* (2013.01); *A61F 2230/0021* (2013.01); *A61F 2250/001* (2013.01); *A61F 2250/0031* (2013.01); *A61M 2025/0004* (2013.01)

(56) References Cited

U.S. PATENT DOCUMENTS

| | | | |
|---|---|---|---|
| 6,383,219 B1 * | 5/2002 | Telandro ............. | A61F 9/00781 623/4.1 |
| 8,888,734 B2 * | 11/2014 | Nissan ................ | A61F 9/00781 604/9 |
| 2007/0191863 A1 | 8/2007 | De Juan et al. | |
| 2019/0046696 A1 * | 2/2019 | Parikh ................ | A61F 9/00781 |

FOREIGN PATENT DOCUMENTS

| | | |
|---|---|---|
| KR | 10-0323807 B1 | 2/2002 |
| KR | 10-2012-0064679 A | 6/2012 |
| KR | 10-2016-0108469 A | 9/2016 |
| KR | 10-2019-0123348 A | 10/2019 |

* cited by examiner

100

110

120

140

110, 120

100'

AQUEOUS HUMOR DRAINAGE DEVICE WITH ADJUSTABLE TUBE DIAMETER

TECHNICAL FIELD

The present invention relates to an aqueous humor drainage device with an adjustable tube diameter, and more specifically, to an aqueous humor drainage device with an adjustable tube diameter where an inner diameter of an inner tube part, which is made of a biodegradable material, is changed.

BACKGROUND ART

Aqueous humor is a fluid which fills an anterior chamber of an eye and contributes to the intraocular pressure or the fluid pressure in the eye. Glaucoma is a progressive eye disease characterized by an increase in intraocular pressure in an eye. The increase in intraocular pressure is mainly caused from insufficient drainage of aqueous humor. Further, a continuous increase in intraocular pressure can cause a permanent vision loss to a glaucoma patient.

Consequently, a glaucoma patient receives a medical treatment focusing on slowing the progression of glaucoma by lowering the intraocular pressure.

The medical treatment starts from a medicine treatment of applying eye drops into an eyeball, and the eye drops are to be applied throughout the rest of life since complete cure of the glaucoma is not possible; however, the medicine treatment can cause several eye-related side effects such as bloodshot eyes, eye pain, allergic conjunctivitis, blurred vision, or deepening of upper eyelid sulcus, or physical side effects such as aggravation of a heart or lung disease, and thus the medicine treatment cannot be continued in many cases. When every attempt of available medicine treatment failed to sufficiently lower the intraocular pressure of a glaucoma patient, glaucoma surgery has to be performed.

Patients who undergo the glaucoma surgery suffer terminal-stage damage to the field of vision in many cases, and thus unsuccessful surgery increases a possibility of immediate blindness.

In addition, the conventional trabeculectomy turns out to be unsuccessful over time after surgery in many cases, and has a high possibility of causing complications. Hence, the aqueous humor drainage device implant surgery has attracted attention and plays a significant role particularly for incurable glaucoma.

However, only 25% of the above-described aqueous humor drainage device implant surgery is reported to be completely successful after five years. In addition, a problem arises in that about 40% of patients have to receive medicine treatment together to adjust the intraocular pressure, and then approximately 30% of patients have to undergo additional surgery.

One of the most important reasons why the glaucoma surgery cannot replace the medicine treatment is that there is a high incidence rate of initial complications and that incision formed in the eye during glaucoma surgery initially causes the aqueous humor (water) in the eye to be suddenly drained, thereby decreasing intraocular pressure like a deflated ball and, if severe, vision is lost due to tissue swelling in an eye. When a diameter of a tube used in the aqueous humor drainage device implant surgery is to large, the risk of ocular hypotonia after surgery is particularly high. Thus a tube having a diameter slightly smaller than that of a conventional tube used in the surgery can inhibit initial complications from developing. However, after a certain period of wound healing reaction after the surgery, a tube having a slightly large diameter enables appropriately low intraocular pressure to be maintained after the surgery.

Consequently, there is a demand for a technology that enables a tube to have a variable diameter depending on a state before or after surgery of the aqueous humor drainage device implant surgery.

(Patent Literature 1) Korean Unexamined Patent Publication No. 10-2019-0123348 (Oct. 31, 2019)

(Patent Literature 2) Korean Patent Registration No. 10-0323807 (Jan. 25, 2002)

SUMMARY OF INVENTION

Technical Problem

An object of the present invention to solve such problems described above is to provide an aqueous humor drainage device with an adjustable tube diameter, the aqueous humor drainage device including an inner tube part made of a biodegradable material so as to provide a shrinkage hole having a diameter of 100 µm during glaucoma surgery and provide the shrinkage hole having a diameter of 300 µm after the glaucoma surgery as the inner tube part biodegrades by aqueous humor.

Technical objects to be achieved by the present invention are not limited to the technical objects mentioned above, and the following description enables other unmentioned technical objects to be clearly understood by a person of ordinary skill in the art to which the present invention pertains.

Solution to Problem

According to a configuration of the present invention to achieve the object described above, there is provided an aqueous humor drainage device with an adjustable tube diameter that is inserted into an eyeball to drain aqueous humor discharged from the eyeball to the outside, the aqueous humor drainage device comprising: an annular outer tube part having a predetermined thickness and having a hollow inside; and an annular inner tube part coupled to an inner surface of the outer tube part and having a predetermined thickness and a hollow inside. The inner tube part has a shrinkage hole formed thereinside and is made of a biodegradable material.

In addition, according to a configuration of the present invention to achieve the object described above, there is provided an aqueous humor drainage device with an adjustable tube diameter that is inserted into an eyeball to drain aqueous humor discharged from the eyeball to the outside, the aqueous humor drainage device comprising: an polyhedral outer tube part having a predetermined thickness and having a hollow inside; and an polyhedral inner tube part coupled to an inner surface of the outer tube part and having a predetermined thickness and a hollow inside. The inner tube part has a shrinkage hole formed thereinside and is made of a biodegradable material.

In the embodiments of the present invention, the inner tube part may biodegrade by the aqueous humor, and a diameter of the shrinkage hole may be increased as the inner tube part biodegrades.

In the embodiment of the present invention, an inner diameter of the inner tube part and an outer diameter of the shrinkage hole may be 100 µm.

In the embodiment of the present invention, when the inner tube part biodegrades by the aqueous humor, an outer diameter of the shrinkage hole may be increased from 100 µm to 300 µm.

In the embodiment of the present invention, an outer diameter of the inner tube part may be 300 µm.

In the embodiment of the present invention, the inner tube part may be made of any one of polycaprolactone (PCL) and polymer (PLGA).

In the embodiment of the present invention, an outer diameter of the outer tube part may be 600 µm.

In the embodiment of the present invention, the outer tube part may be made of polydimethylsiloxane (PDMS).

In one embodiment of the present invention, the outer tube part and the inner tube part may be open at both sides, and the outer tube part may have a curved outer surface.

In the other embodiment of the present invention, the outer tube part and the inner tube part may be open at both sides, and an edge between contiguous outer surfaces of outer surfaces of the outer tube part may be rounded.

Advantageous Effects of Invention

The present invention according to the above-described configurations is effective in that an inner tube part is made of a biodegradable material so as to provide a shrinkage hole having a diameter of 100 µm during glaucoma surgery and provide the shrinkage hole having a diameter of 300 µm after the glaucoma surgery as the inner tube part biodegrades by aqueous humor, and thus frequent occurrence of ocular hypotonia and ocular hypertension before and after the glaucoma surgery can be minimized.

The effect of the present invention is construed not to be limited to the above-described effect but to include every effect that can be derived from the configurations of the present invention described in detailed description or claims of the present invention.

4

Figure 12:
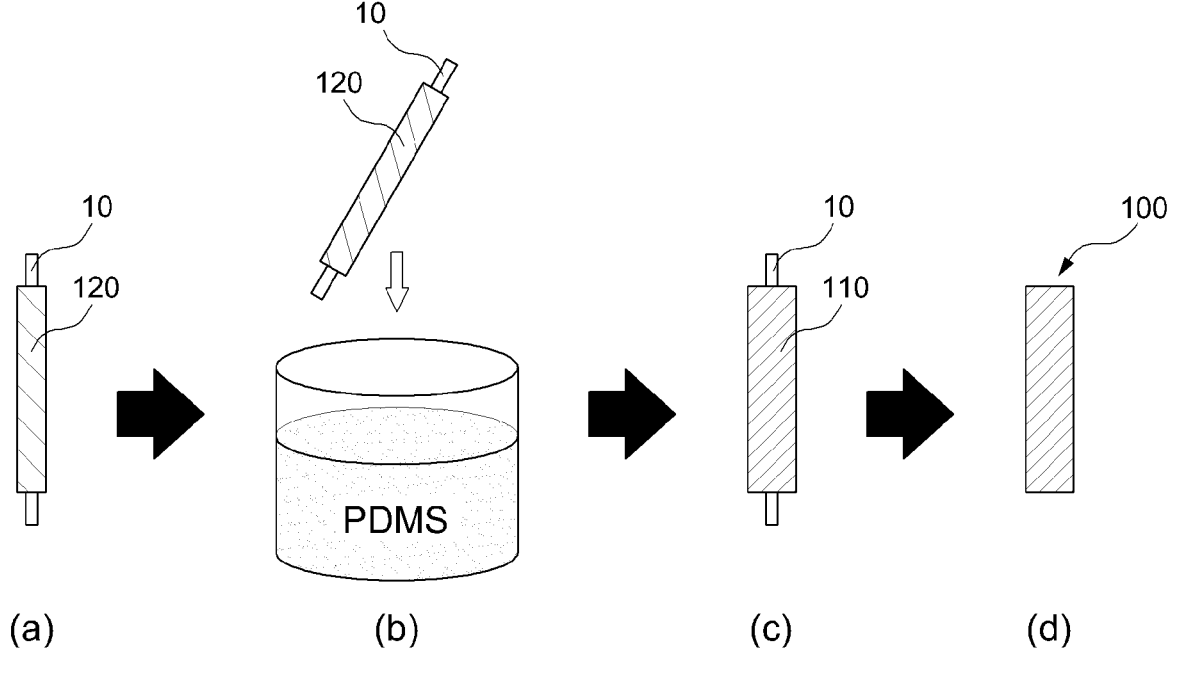

FIG. 12 are views illustrating a method for manufacturing the aqueous humor drainage device with an adjustable tube diameter according to the first embodiment of the present invention.

Figure 13:
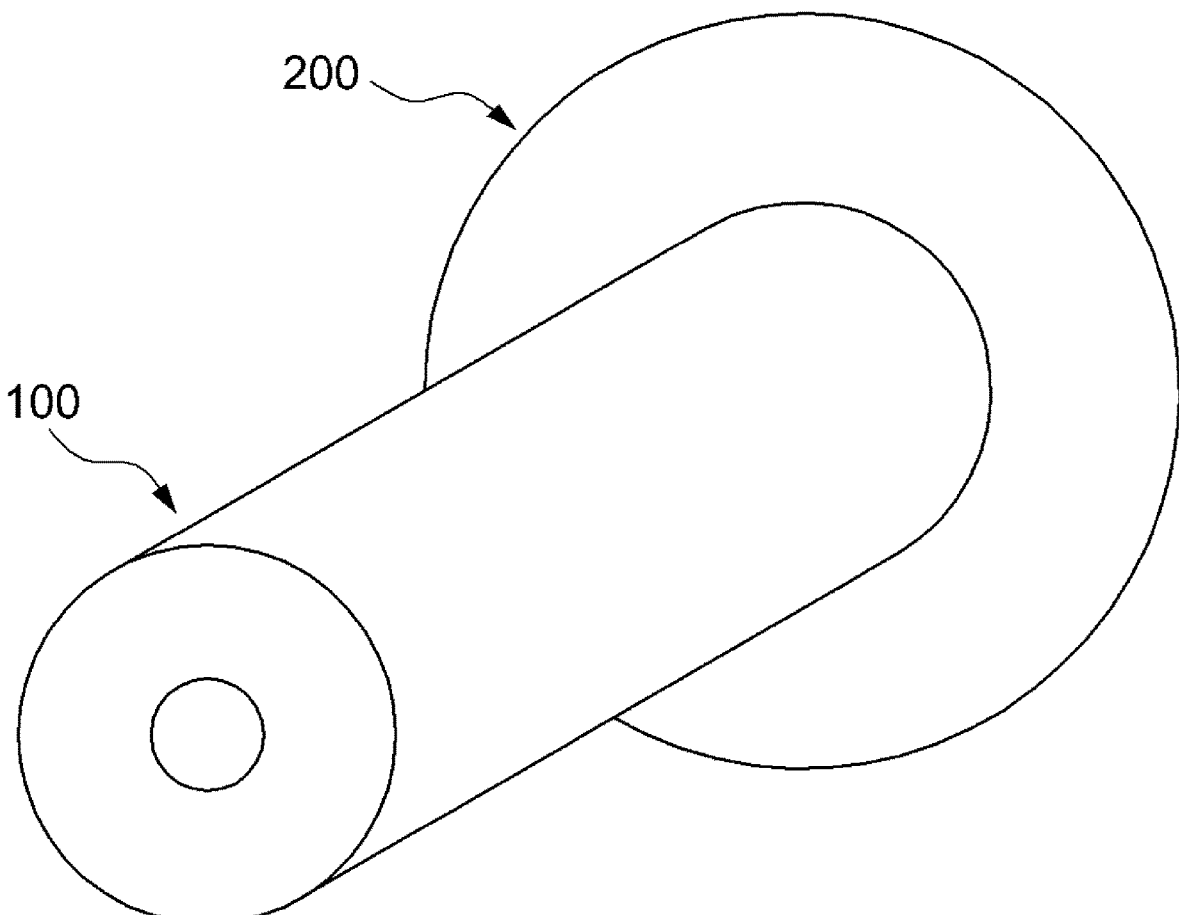

FIG. 13 is a one-directional perspective view illustrating a state in which a ring-shaped support is coupled to the aqueous humor drainage device with an adjustable tube diameter according to the first embodiment of the present invention.

Figure 14:
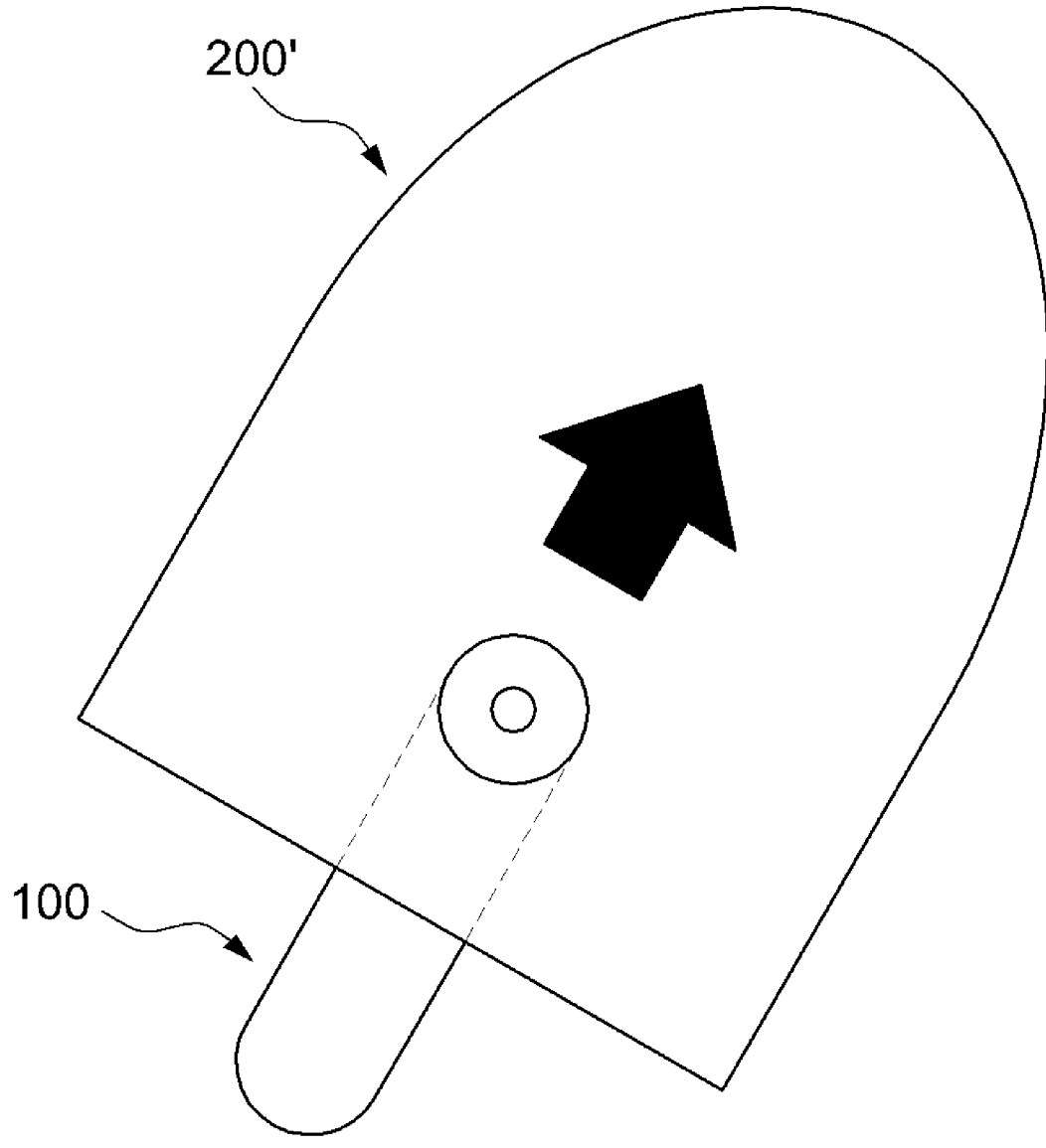

FIG. 14 is a one-directional perspective view illustrating a state in which a support, which is an endplate, is coupled to the aqueous humor drainage device with an adjustable tube diameter according to the first embodiment of the present invention.

DESCRIPTION OF EMBODIMENTS

According to the preferred embodiment of the present invention, there is provided a aqueous humor drainage device with an adjustable tube diameter that is inserted into an eyeball to drain aqueous humor discharged from the eyeball to the outside, the aqueous humor drainage device comprising: an annular outer tube part having a predetermined thickness and having a hollow inside; and an annular inner tube part coupled to an inner surface of the outer tube part and having a predetermined thickness and a hollow inside. The inner tube part has a shrinkage hole thereinside and is made of a biodegradable material.

Embodiments

Hereinafter, the present invention will be described with reference to the accompanying drawings. However, the present invention can be realized as various different examples, thus not being limited to the embodiments described here. Besides, a part unrelated to the description is omitted from the drawings in order to clearly illustrate the present invention, and similar reference signs are assigned to similar parts through the entire specification.

In the entire specification, a case where a certain part "is connected to (accesses, is in contact with, or is coupled to)" another part means not only a case where the parts are "directly connected" to each other, but also a case where the parts are "indirectly connected" to each other with another member interposed therebetween. In addition, when a certain part "comprises" a certain configurational element, this means that another configurational element is not excluded but the configurational element can be further included unless specifically described otherwise.

Terms used in this specification are used to describe only a specific embodiment and are not intentionally used to limit the present invention thereto. A word having a singular form also includes a meaning of its plural form unless obviously implied otherwise in context. In this specification, a term such as "to comprise" or "to have" is construed to specify that a feature, a number, a step, an operation, a configurational element, a part, or a combination thereof described in the specification is present and not to exclude presence or a possibility of addition of one or more other features, numbers, steps, operations, configurational elements, parts, or combinations thereof in advance.

Hereinafter, embodiments of the present invention will be described in detail with reference to the accompanying drawings.

1. First Embodiment

Hereinafter, an aqueous humor drainage device with an adjustable tube diameter according to a first embodiment of the present invention will be described with reference to FIGS. 1 to 6.

Figure 1:
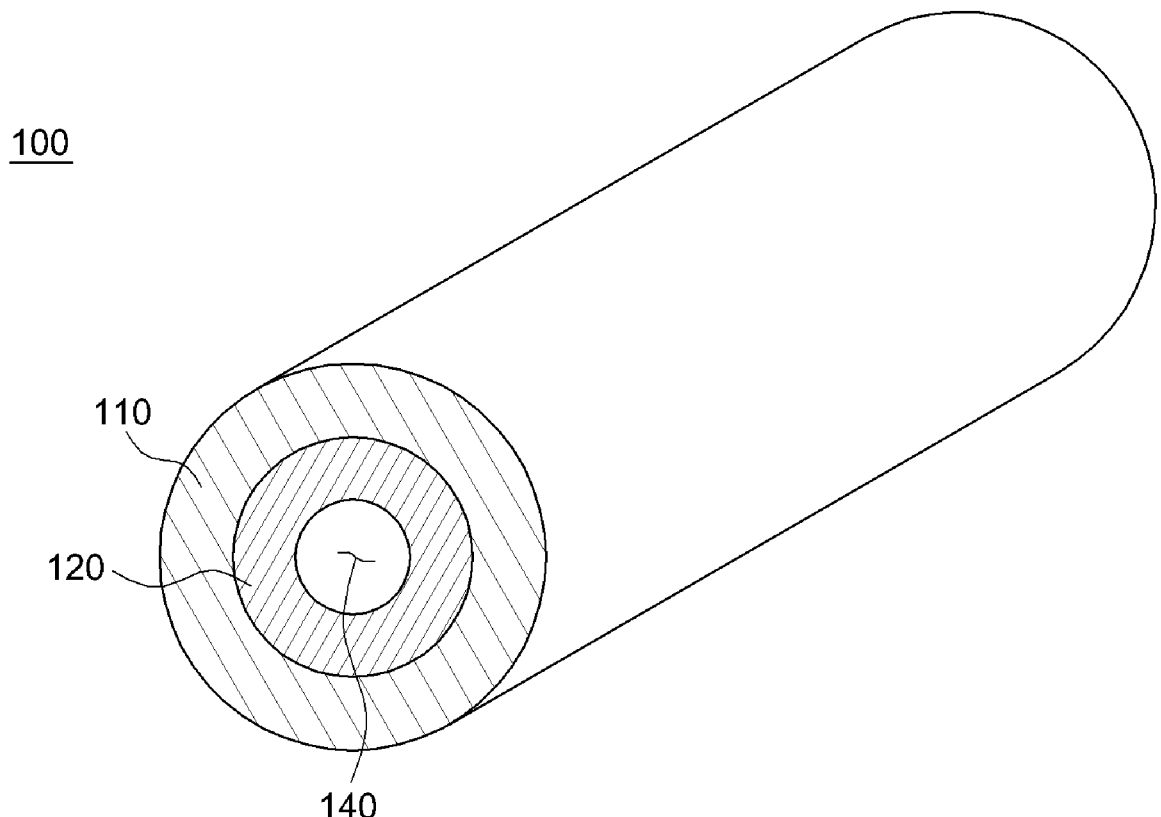
FIG. 1 is a one-directional perspective view illustrating an aqueous humor drainage device with an adjustable tube diameter according to a first embodiment of the present invention.
Figure 2:
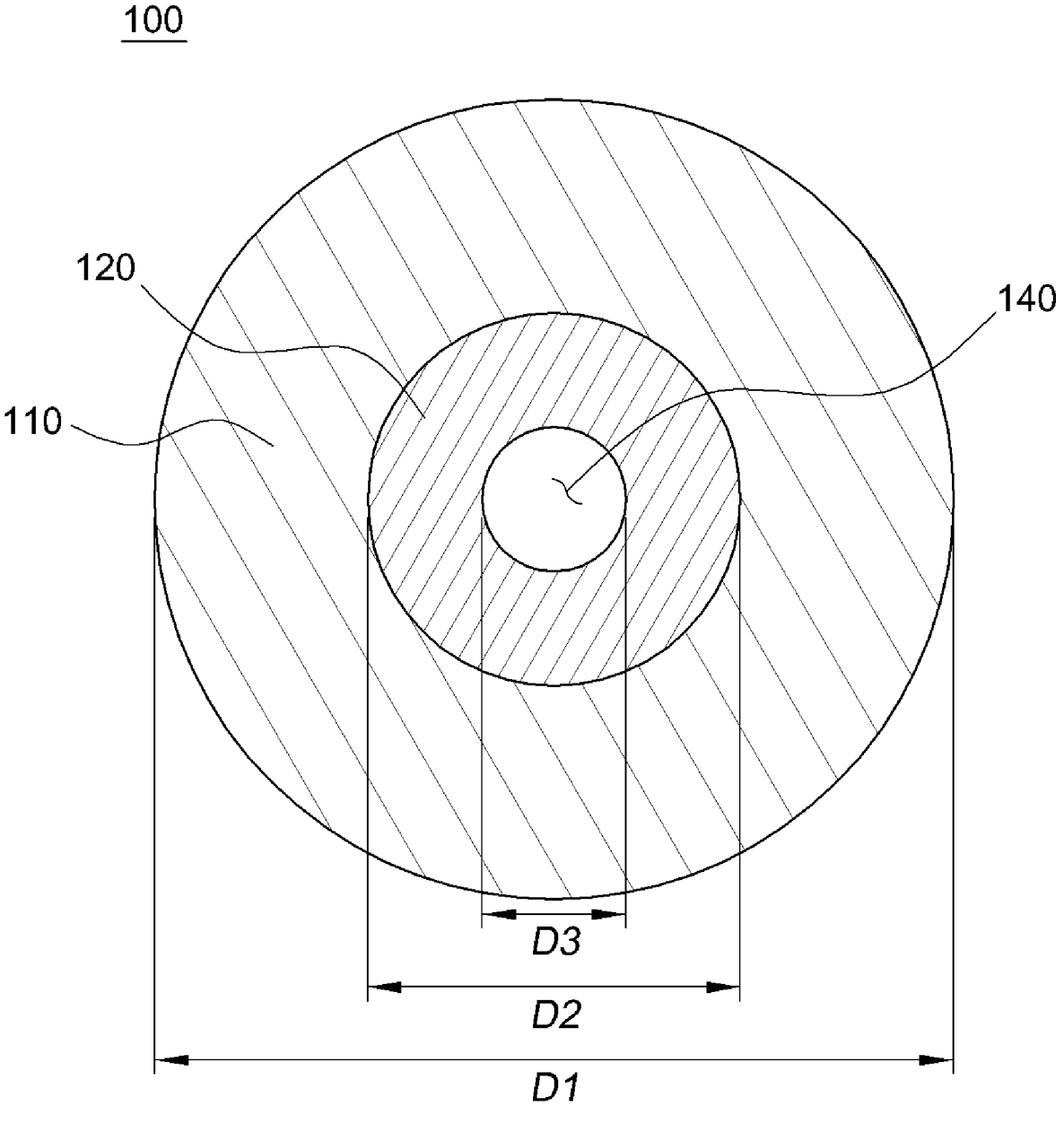
FIG. 2 is a front view of FIG. 1.

FIG. 1 is a one-directional perspective view illustrating an aqueous humor drainage device with an adjustable tube diameter according to a first embodiment of the present invention. FIG. 2 is a front view of FIG. 1.

With reference to FIGS. 1 and 2, an aqueous humor drainage device with an adjustable tube diameter 100 according to the first embodiment of the present invention is inserted into an eyeball to drain aqueous humor discharged from the eyeball to the outside, and the aqueous humor drainage device includes an outer tube part 110, an inner tube part 120, and a shrinkage hole 140.

The outer tube part 110 can have a predetermined thickness and can have an annular shape with a hollow inside. Specifically, the outer tube part 110 can have a tube shape which is open at both sides, and the outer tube part 110 can have a curved outer surface.

In addition, the outer tube part 110 can be made of polydimethylsiloxane (PDMS), thereby being fixed to the eyeball without deformation even when being inserted into the eyeball.

Figure 3:
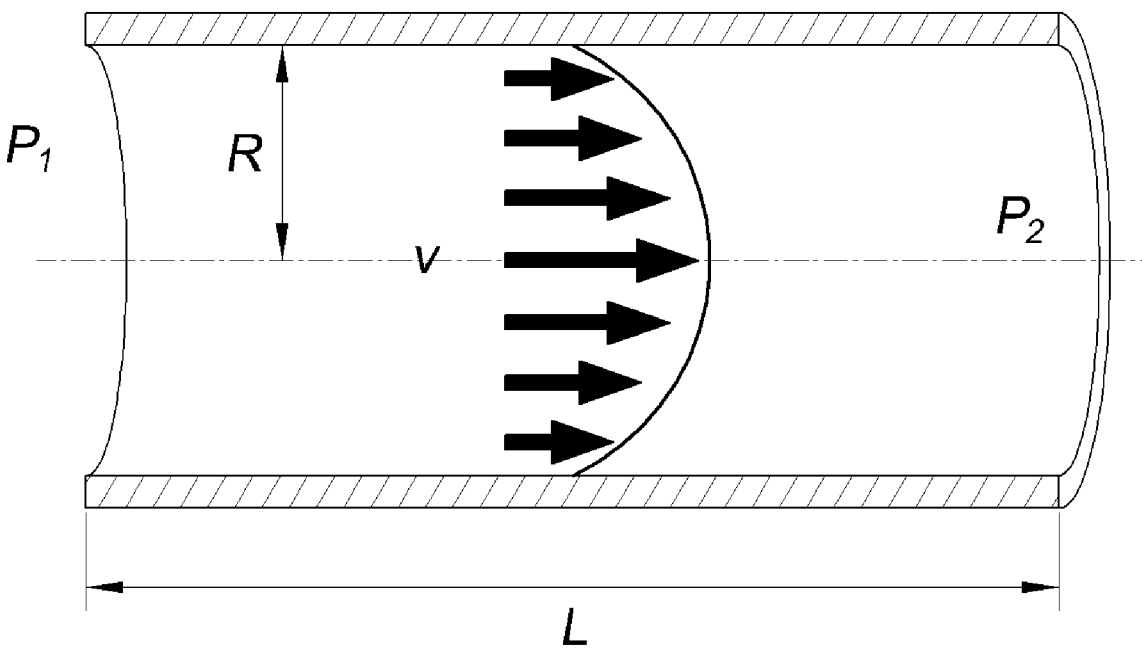
FIG. 3 is a conceptual diagram illustrating a tube pressure, a flow velocity, and a radius of a common tube to which a flow rate for designing the aqueous humor drainage device with an adjustable tube diameter according to the first embodiment of the present invention is applied.

FIG. 3 is a conceptual diagram illustrating a tube pressure, a flow velocity, and a radius of a common tube to which a flow rate for designing the aqueous humor drainage device with an adjustable tube diameter according to the first embodiment of the present invention is applied.

With reference to FIG. 3, a flow rate is determined by Equation 1 in accordance with Poiseuille's law, and a difference between pressures P1 and P2 measured at both ends of a tube is inversely proportional to a tube diameter to the power of 4, thus being significantly affected by the diameter of the tube.

$$Q = \frac{\pi P r^4}{8 \eta l} \qquad \text{Equation 1}$$

(Q: flow rate, P: pressure, r: radius, η: flow velocity, L: length of tube)

In the glaucoma surgery, an Ahmed glaucoma valve is used as an aqueous humor drainage device with a body which is the only one currently available in South Korea. When an inner diameter of a tube in the Ahmed glaucoma valve is 300 μm, the flow rate of aqueous humor discharged from an eyeball is 2 μl/min, and the flow velocity is 0.932 cP (water at 23° C.), a difference between pressures P1 and P2 measured at both ends of the tube is about 0.002 mmHg.

Consequently, ocular hypotonia (<6 mmHg) occurs immediately after the glaucoma surgery.

In the present invention to solve the ocular hypotonia, an inner tube part 120 having a diameter D3 of 100 μm smaller than a diameter D2 of 300 μm is used to increase internal resistance of the tube, and thereby the overfiltration of aqueous humor is reduced so as to reduce the occurrence of ocular hypotonia.

In order to realize this, the inner tube part 120 is formed of a biodegradable material. Specifically, the inner tube part 120 is made of a biodegradable material. For example, the inner tube part 120 is made of any one of polycaprolactone (PCL) and polymer (PLGA).

In accordance with Equation 1 described above, an outer diameter D1 of the outer tube part 110 is desirably 600 μm; however, the diameter thereof is not limited thereto.

The inner tube part 120 can be coupled to an inner surface of the outer tube part 110, can have a predetermined thickness, and can have an annular shape with a hollow inside.

The inner tube part 120 has a shrinkage hole 140 as an empty space therein, and a diameter of the shrinkage hole 140 is changed depending on the inner tube part 120 which is in contact with the aqueous humor.

In this respect, as the inner tube part 120 biodegrades by the aqueous humor, the diameter of the shrinkage hole 140 is increased, which will be described below in detail.

In accordance with Equation 1 described above, an outer diameter D2 of the inner tube part 120 is desirably 300 μm; however, the diameter thereof is not limited thereto.

The outer tube part 110 and the inner tube part 120 can be open at both sides and can have a hollow tube shape.

The shrinkage hole 140 is an empty inner space of the inner tube part 120 and can have a round columnar shape.

In addition, an inner diameter D1 of the inner tube part 120 and an outer diameter D1 of the shrinkage hole 140 can be 100 μm.

The diameter of the shrinkage hole 140 is increased as the inner tube part 120 biodegrades. Specifically, when the inner tube part 120 biodegrades by the aqueous humor, the outer diameter of the shrinkage hole 140 is increased from 100 μm to 300 μm.

Since the inner tube part 120 and the shrinkage hole 140 have a diameter of 100 μm during the glaucoma surgery, the occurrence of ocular hypotonia is minimized.

In addition, when a certain period of time elapses after the surgery, the inner tube part 120 biodegrades due to contact with the aqueous humor discharged from the eyeball, and thus the outer diameter of the shrinkage hole 140 is increased from 100 μm to 300 μm. Hence, the occurrence of ocular hypertension due to fibrosis progression of a filtering bleb is minimized.

Figure 4:
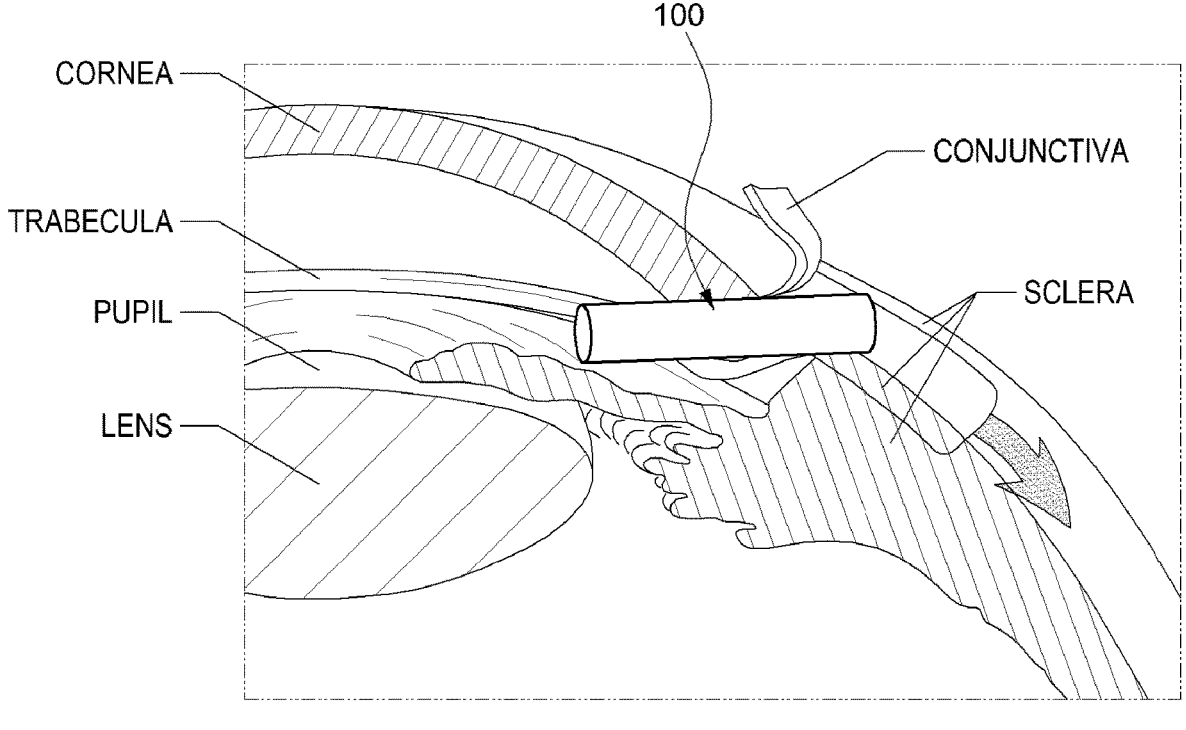
FIG. 4 is perspective view illustrating a state in which the aqueous humor drainage device with an adjustable tube diameter is inserted into an eyeball according to the first embodiment of the present invention.

FIG. 4 is perspective view illustrating a state in which the aqueous humor drainage device with an adjustable tube diameter is inserted into an eyeball according to the first embodiment of the present invention.

As illustrated in FIG. 4, an eyeball consists of a cornea, a conjunctiva, a sclera, a trabecula, a pupil, a lens, and the like.

As illustrated in FIG. 4, the aqueous humor drainage device with an adjustable tube diameter 100 according to the first embodiment of the present invention can be inserted into an anterior chamber through the conjunctiva and the sclera. FIG. 4 illustrates an exemplary view for the description, and an insertion location of the present invention can be changed depending on a lesion location.

Figure 5:
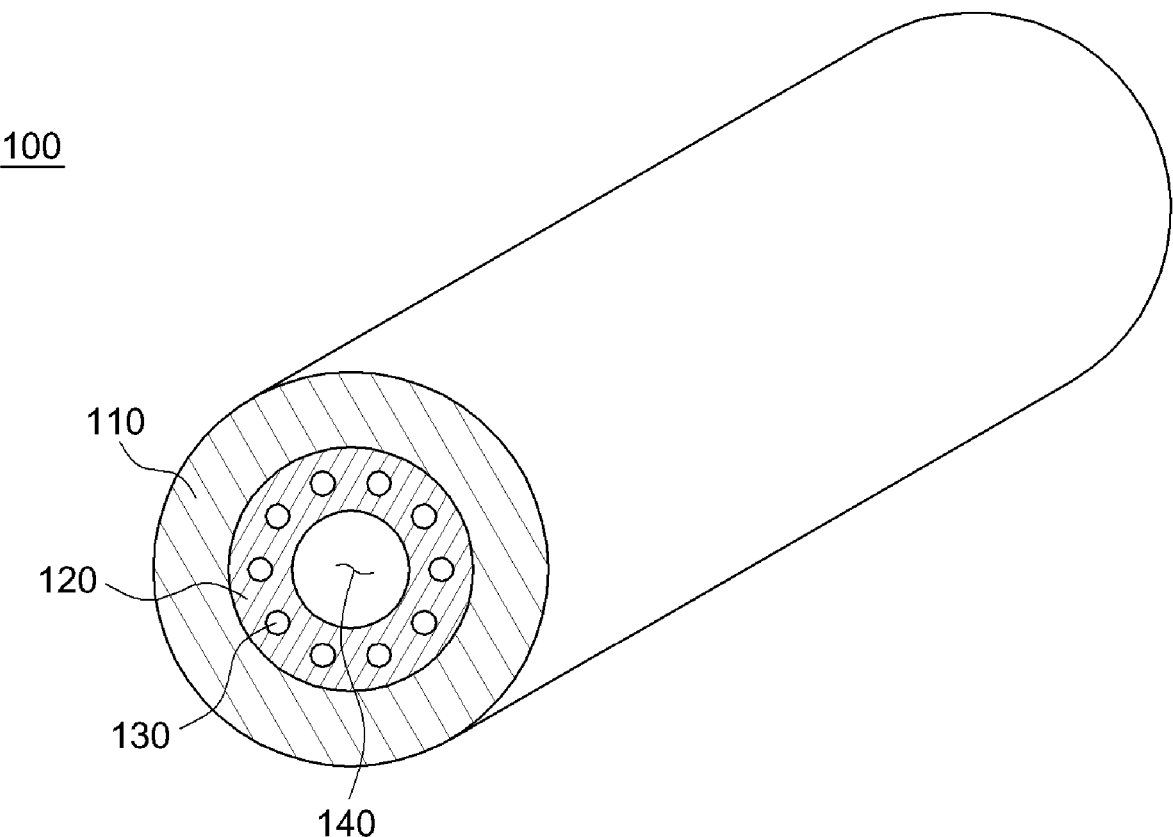
FIG. 5 is a perspective view illustrating a modification example of the first embodiment of the present invention.
Figure 6:
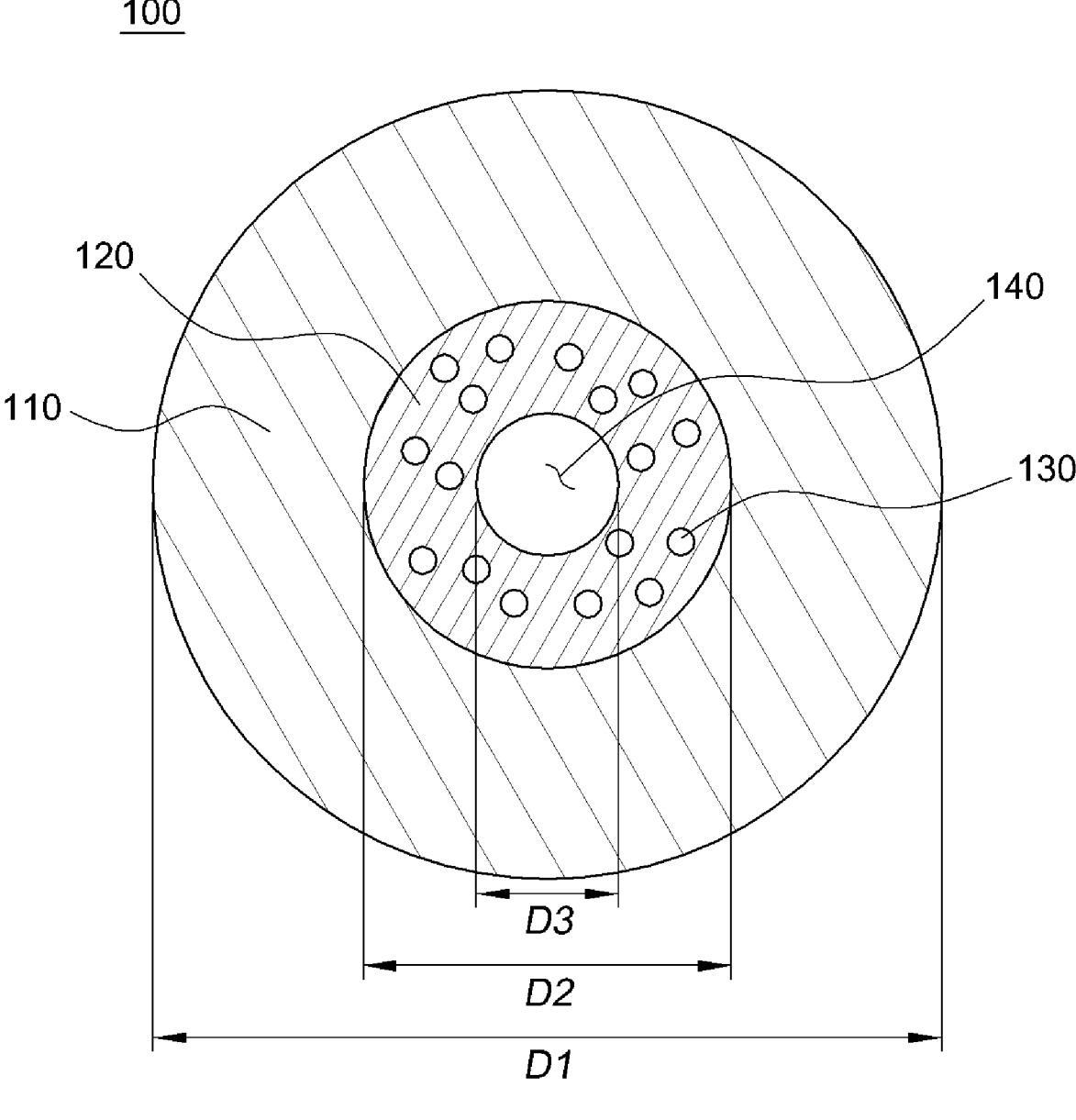
FIG. 6 is a front view of FIG. 5.

FIG. 5 is a perspective view illustrating a modification example of the first embodiment of the present invention. FIG. 6 is a front view of FIG. 5.

The present invention can be configured as illustrated in FIGS. 5 and 6 as a modification example of the first embodiment.

The aqueous humor drainage device with an adjustable tube diameter 100 according to the modification example of the first embodiment of the present invention includes an outer tube part 110, an inner tube part 120, a porous portion 130, and a shrinkage hole 140, further adding only the porous portion 130 to the configurational elements of the first embodiment.

With reference to FIGS. 5 and 6, the porous portion 130 is formed in the inner tube part 120 having the predetermined thickness and is open at both sides.

A drug (antifibrotic drug) can be injected into the porous portion 130 having the above-described structure.

2. Second Embodiment

Hereinafter, an aqueous humor drainage device with an adjustable tube diameter according to a second embodiment of the present invention will be described with reference to FIGS. 7 to 10; however, the description provided above will be referred to for technical details common to those of the configurational elements of the first embodiment, and technical details different from those of the configurational elements of the first embodiment will be specifically described.

An aqueous humor drainage device with an adjustable tube diameter 100' according to the second embodiment of the present invention has the same technical characteristics as those of the first embodiment except that shapes of an outer tube part 110', an inner tube part 120', and a shrinkage hole 140' are only different from those of the configurational elements of the first embodiment.

Figure 7:
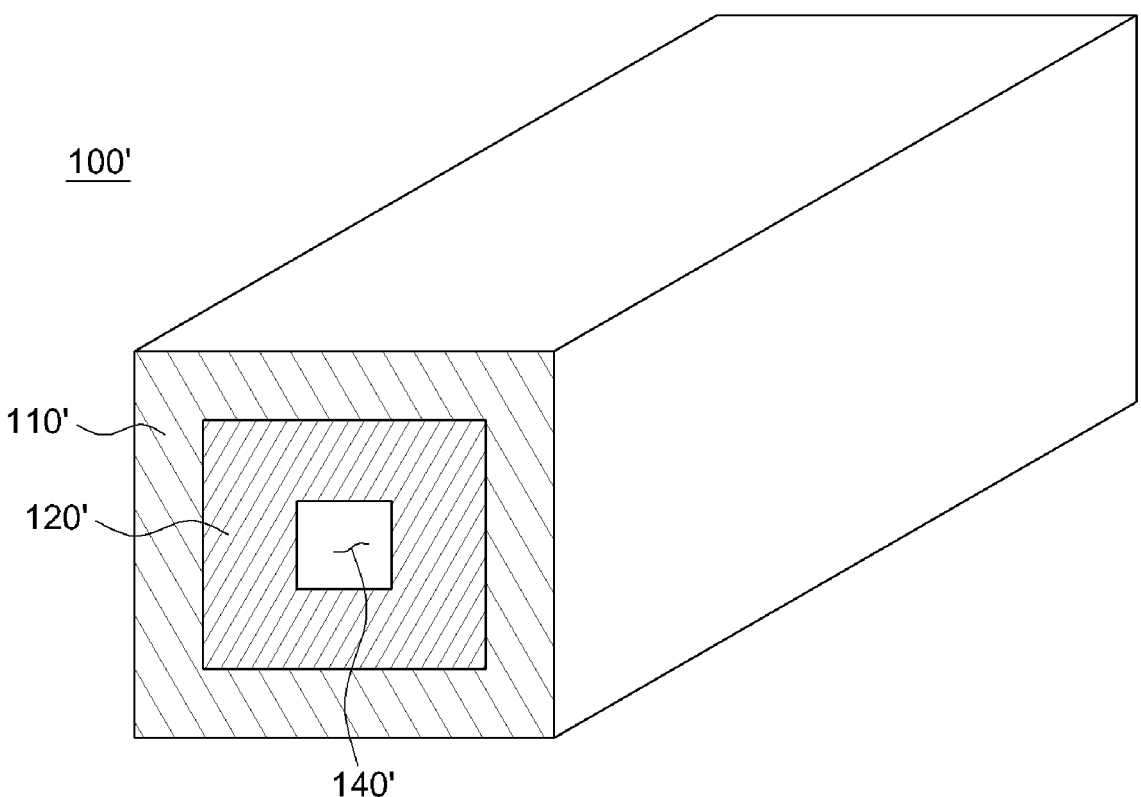
FIG. 7 is a one-directional perspective view illustrating an aqueous humor drainage device with an adjustable tube diameter according to a second embodiment of the present invention.
Figure 8:
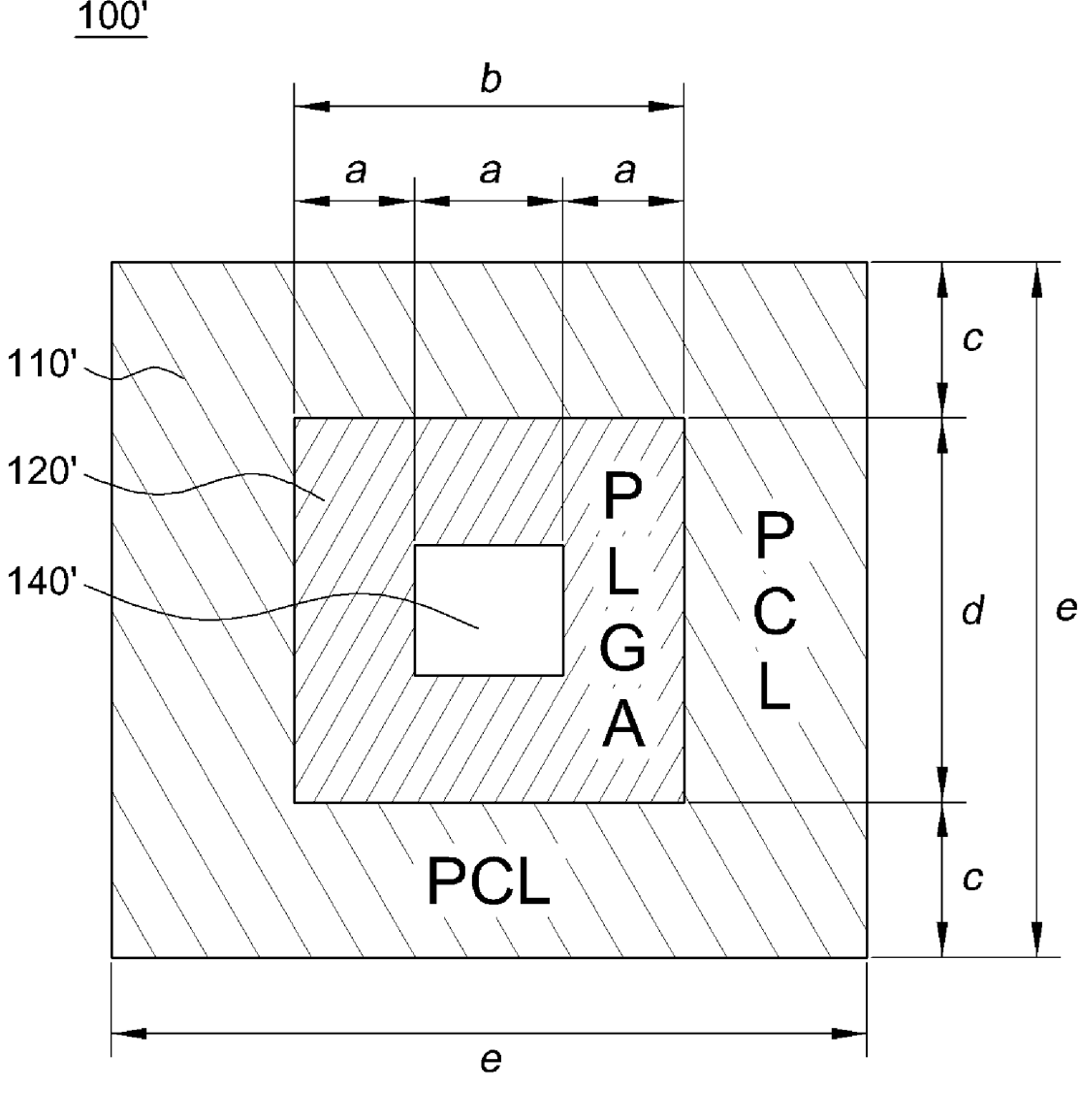
FIG. 8 is a front view of FIG. 7.

FIG. 7 is a one-directional perspective view illustrating the aqueous humor drainage device with an adjustable tube diameter according to the second embodiment of the present invention. FIG. 8 is a front view of FIG. 7.

The aqueous humor drainage device with an adjustable tube diameter 100' according to the second embodiment of the present invention is inserted into an eyeball to drain aqueous humor discharged from the eyeball to the outside, and the aqueous humor drainage device 100' includes the outer tube part 110', the inner tube part 120', and the shrinkage hole 140'.

The outer tube part 110' can have a predetermined thickness and can have a polyhedral shape with a hollow inside. Specifically, with reference to FIGS. 7 and 8, the outer tube part 110' can have a rectangular tube shape.

In addition, with reference to FIG. 8, an outer horizontal length e and an outer vertical length e of the outer tube part 110' are both 600 μm, a thickness c of the outer tube part 110' is 150 μm, and an inner horizontal length b and an inner vertical length d of the outer tube part 110' are both 300 μm.

The inner tube part 120' can be coupled to an inner surface of the outer tube part 110', can have a predetermined thickness, and can have the polyhedral shape with a hollow inside. Specifically, with reference to FIGS. 7 and 8, the inner tube part 120' can have a rectangular tube shape and is formed to correspond to the outer tube part 110' while being smaller than the outer tube part 110'.

Desirably, the outer tube part 110' and the inner tube part 120' are open at both sides, and an edge between contiguous outer surfaces of outer surfaces of the outer tube part 120' is rounded.

In addition, with reference to FIG. 8, an outer horizontal length b and an outer vertical length d of the inner tube part 120' are both 300 μm, and an inner horizontal length b and an inner vertical length a of the inner tube part 120' are both 100 μm.

In addition, the inner tube part 120' has the shrinkage hole 140' therein, and the inner tube part 120' is made of a biodegradable material.

The shrinkage hole 140' is an empty space in the inner tube part 120' and can have a rectangular shape.

Figure 9:
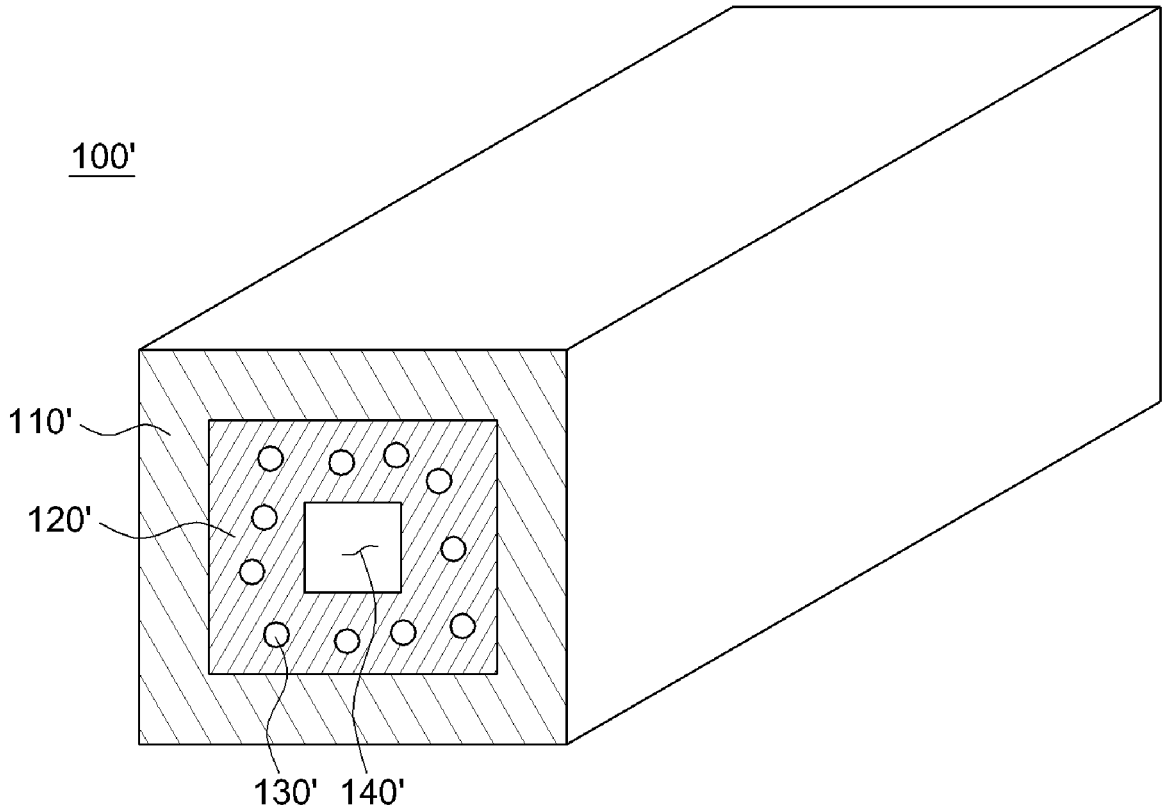
FIG. 9 is a one-directional perspective view illustrating a modification example of the second embodiment of the present invention.
Figure 10:
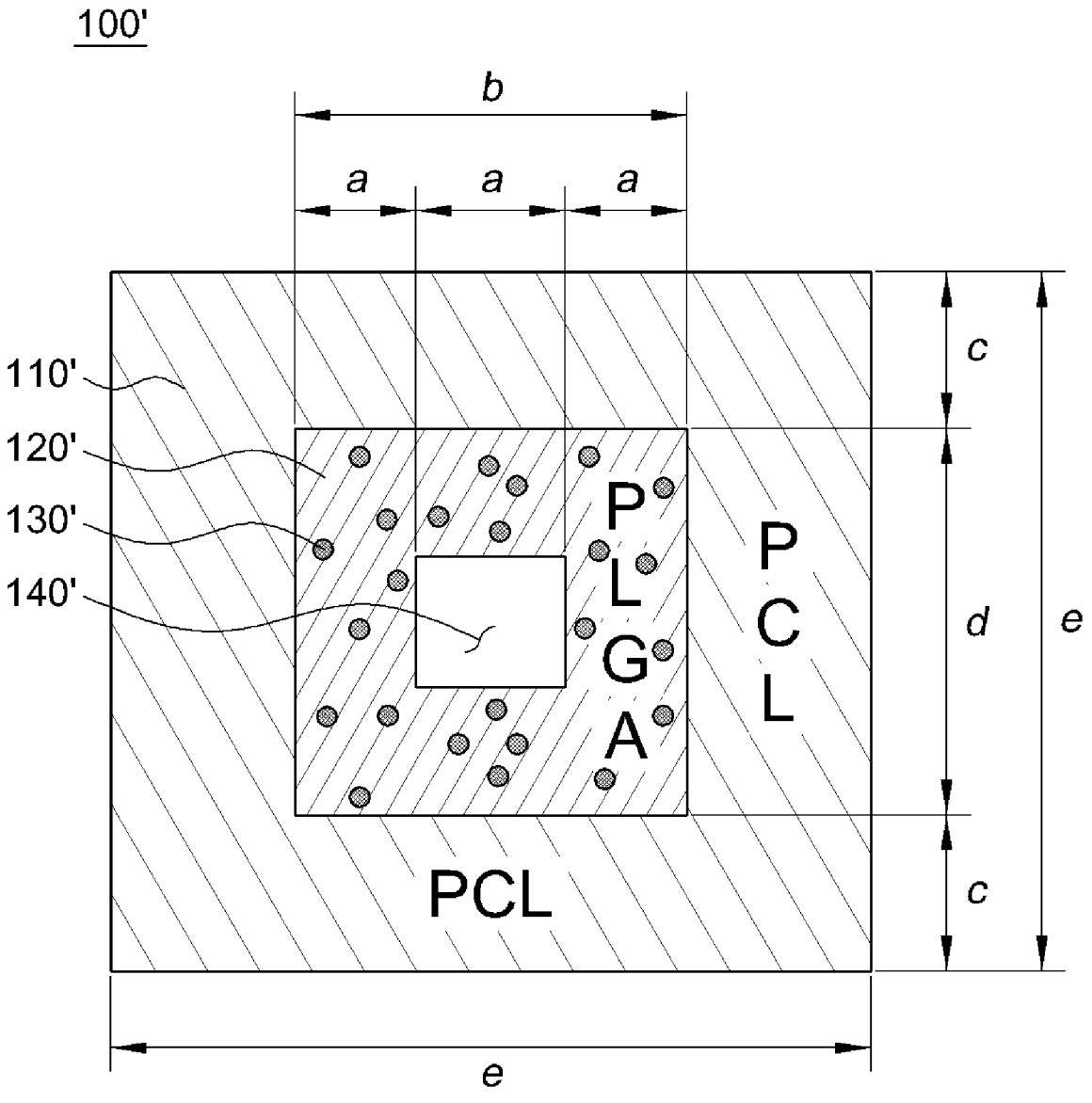
FIG. 10 is a front view of FIG. 9.

The present invention can be configured as illustrated in FIGS. 9 and 10 as a modification example of the second embodiment.

FIG. 9 is a one-directional perspective view illustrating the modification example of the second embodiment of the present invention. FIG. 10 is a front view of FIG. 9.

The aqueous humor drainage device with an adjustable tube diameter 100' according to the modification example of the second embodiment of the present invention includes an outer tube part 110', an inner tube part 120', a porous portion 130', and a shrinkage hole 140', further adding only the porous portion 130' to the configurational elements of the second embodiment.

With reference to FIGS. 9 and 10, the porous portion 130' is formed in the inner tube part 120' having the predetermined thickness and is open at both sides.

A drug (antifibrotic drug) can be injected into the porous portion 130' having the above-described structure.

Figure 11:
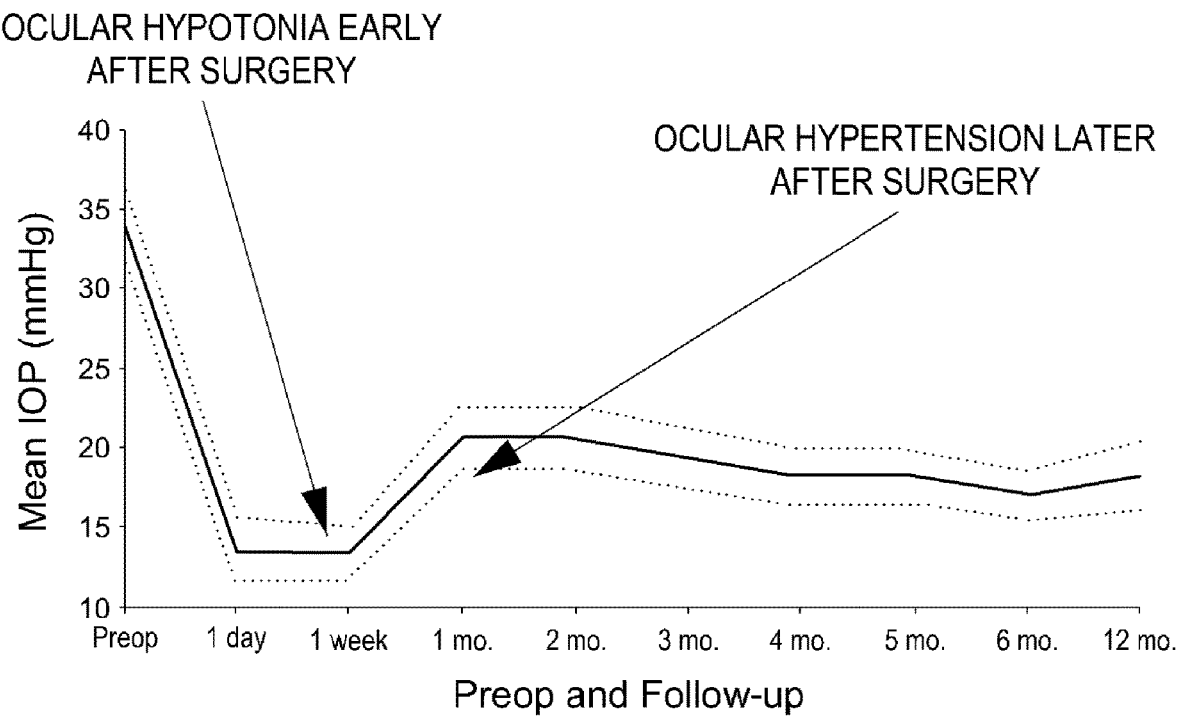
FIG. 11 is a graph illustrating a change in intraocular pressure of an eyeball when surgery is performed by a standardized aqueous humor drainage device in the related art.

FIG. 11 is a graph illustrating a change in intraocular pressure of an eyeball when surgery is performed by a standardized aqueous humor drainage device in the related art.

As illustrated in FIG. 11, ocular hypotonia occurs early in the glaucoma surgery, and ocular hypertension occurs when a certain period of time elapses after the surgery.

Hence, according to the present invention, since the inner tube part 120 has the inner diameter of 100 μm during the surgery, the occurrence of the ocular hypotonia is minimized. In addition, when a certain period of time elapses after the surgery, the inner tube part 120 which is in contact with the aqueous humor of the eyeball biodegrades such that the outer diameter of the shrinkage hole 140 is increased to 300 μm, and thus the occurrence of ocular hypertension is minimized.

(a), (b), (c), and (d) of FIG. 12 are views illustrating a method for manufacturing the aqueous humor drainage device with an adjustable tube diameter according to the first embodiment of the present invention.

The method for manufacturing the aqueous humor drainage device with an adjustable tube diameter according to the first embodiment of the present invention includes inserting a needle 10 into the inner tube part 120 (refer to (a) of FIG. 12) and then coating the inner tube part by immersing the needle 10 and the inner tube part 120 in a container containing PDMS (refer to (b) of FIG. 12).

Next, the needle 10 and the coated inner tube part 120 are baked at 50° C. for 12 hours (refer to (c) of FIG. 12), then the needle is removed, and the aqueous humor drainage device with an adjustable tube diameter 100 of the present invention is manufactured (refer to (d) of FIG. 12).

The manufacturing method is equally applied to not only the first embodiment but also the second embodiment and the modification examples of the respective embodiments.

FIG. 13 is a one-directional perspective view illustrating a state in which a ring-shaped support is coupled to the aqueous humor drainage device with an adjustable tube diameter according to the first embodiment of the present invention.

As illustrated in FIG. 13, the aqueous humor drainage device with an adjustable tube diameter 100 according to the first embodiment of the present invention can be coupled to a support 200.

Specifically, the ring-shaped support 200 formed to have a diameter larger than that of the outer tube part 110 can be coupled to an outer circumferential surface at one side of the outer tube part 110 of the aqueous humor drainage device 100.

The support 200 is settled on a surface of the eyeball to support the aqueous humor drainage device 100 such that the aqueous humor drainage device 100 is not inserted further deep into the eyeball after the aqueous humor drainage device is inserted into the eyeball.

In addition, the support 200 is equally applied to not only the first embodiment but also the second embodiment and the modification examples of the respective embodiments.

FIG. 14 is a one-directional perspective view illustrating a state in which a support, which is an endplate, is coupled to the aqueous humor drainage device with an adjustable tube diameter according to the first embodiment of the present invention.

As illustrated in FIG. 14, the aqueous humor drainage device with an adjustable tube diameter 100 according to the first embodiment of the present invention can be coupled to a support 200'.

Specifically, the support 200', which is the endplate formed to have a width larger than that of the above-described support 200, has a hole, and one side of the outer tube part 110 of the aqueous humor drainage device 100 can be coupled to the support 200' to correspond to the hole.

The support 200' is settled on a surface of the eyeball to support the aqueous humor drainage device 100 such that the aqueous humor drainage device 100 is not inserted further deep into the eyeball after the aqueous humor drainage device is inserted into the eyeball, and the aqueous humor discharged from the eyeball is drained in an arrow direction illustrated in FIG. 14.

In addition, the support 200' is equally applied to not only the first embodiment but also the second embodiment and the modification examples of the respective embodiments.

The description of the present invention described above is provided as an example, and a person of ordinary skill in the art to which the present invention pertains can understand that it is possible to easily modify the present invention to another embodiment without changing the technical idea or the essential feature of the present invention. Therefore, the embodiments described above need to be understood as exemplified embodiments and not as embodiments described to limit the present invention in every aspect. For example, the configurational elements described in a singular forma may be realized in a distributed manner. Similarly, the configurational elements described in distributed manner may be realized in a combined manner.

The scope of the present invention is represented by the claims to be described below, and the meaning and the scope of the claims and every modified or altered examples derived from the equivalent concept of the claims is to be construed to be included in the scope of the present invention.

REFERENCE SIGNS LIST

10: Needle
100, 100': Aqueous humor drainage device with an adjustable tube diameter
110, 110': Outer tube part
120, 120': Inner tube part
130, 130': Porous portion
140, 140': Shrinkage hole
200, 200': Support

The invention claimed is:

1. An aqueous humor drainage device with an adjustable tube diameter that is configured to be inserted into an eyeball to drain aqueous humor discharged from the eyeball to an outside, the aqueous humor drainage device comprising:

an annular outer tube part having a first predetermined thickness and having a hollow inside; and an annular inner tube part coupled to an inner surface of the annular outer tube part and having a second predetermined thickness, the annular inner tube part including a hole therein, the hole extending along an axial direction of the annular inner tube part to be open at two opposite ends of the annular inner tube part, the annular inner tube part further including therein a plurality of porous portions, each pore in the porous portion extending along the axial direction of the annular inner tube part, each porous portion being open at the two opposite ends of the annular inner tube part, the plurality of porous portions surrounding the hole when viewed from a cross-section of the annular inner tube part perpendicular to the axial direction of the annular inner tube part, wherein the annular inner tube part includes a biodegradable material, and wherein a diameter of the hole is greater than a diameter of each porous portion.

2. The aqueous humor drainage device according to claim 1, wherein the annular inner tube part is configured to biodegrade by the aqueous humor, and wherein a diameter of the hole is configured to be increased as the annular inner tube part biodegrades.

3. The aqueous humor drainage device according to claim 2, wherein an inner diameter of the annular inner tube part and an outer diameter of the hole are 100 μm.

4. The aqueous humor drainage device according to claim 3, wherein, when the annular inner tube part biodegrades by the aqueous humor, the outer diameter of the hole is configured to be increased from 100 μm to 300 μm.

5. The aqueous humor drainage device according to claim 1, wherein an outer diameter of the annular inner tube part is 300 μm.

6. The aqueous humor drainage device according to claim 1, wherein the annular inner tube part is made of any one of polycaprolactone (PCL) and polymer (PLGA).

7. The aqueous humor drainage device according to claim 1, wherein an outer diameter of the annular outer tube part is 600 μm.

8. The aqueous humor drainage device according to claim 1, wherein the annular outer tube part is made of polydimethylsiloxane (PDMS).

9. The aqueous humor drainage device according to claim 1, wherein the annular outer tube part and the annular inner tube part are open at both sides, and wherein the annular outer tube part has a curved outer surface.

10. The aqueous humor drainage device according to claim 1, wherein the aqueous humor drainage device is configured to penetrate a conjunctiva to be inserted into an anterior chamber to drain aqueous humor to an outside of the eyeball.

11. An aqueous humor drainage device with an adjustable tube diameter that is configured to be inserted into an eyeball to drain aqueous humor discharged from the eyeball to an outside, the aqueous humor drainage device comprising:

a polyhedral outer tube part having a first predetermined thickness and having a hollow inside;

a polyhedral inner tube part coupled to an inner surface of the polyhedral outer tube part and having a second predetermined thickness, the polyhedral inner tube part including a hole therein, the hole extending along an axial direction of the polyhedral inner tube part to be open at two opposite ends of the polyhedral inner tube part, the polyhedral inner tube part further including therein a plurality of porous portions, each pore in the porous portion extending along the axial direction of the polyhedral inner tube part, each porous portion being open at the two opposite ends of the polyhedral inner tube part, the plurality of porous portions surrounding the hole when viewed from a cross-section of the polyhedral inner tube part perpendicular to the axial direction of the polyhedral inner tube part, wherein the polyhedral inner tube part includes a biodegradable material, and wherein a diameter of the hole is greater than a diameter of each porous portion, wherein the aqueous humor drainage device is configured to penetrate conjunctiva to be inserted into an anterior chamber to drain aqueous humor to outside.

12. The aqueous humor drainage device according to claim 11, wherein the polyhedral outer tube part and the polyhedral inner tube part are open at both opposite ends, and wherein an edge between adjacent outer surfaces of the polyhedral outer tube part is rounded.

13. The aqueous humor drainage device according to claim 11, wherein the aqueous humor drainage device is configured to penetrate a conjunctiva to be inserted into an anterior chamber to drain aqueous humor to an outside of the eyeball.

* * * * *